United States Patent [19]

Jeffreys et al.

[11] 4,055,666
[45] Oct. 25, 1977

[54] ANIMAL FEED YEAST SUPPLEMENT FROM DRIED WHEY YEAST BRAN PROCESS

[75] Inventors: George A. Jeffreys; Jean L. Price; James F. Tobey, all of Salem, Va.

[73] Assignee: George A. Jeffreys & Co., Inc., Salem, Va.

[21] Appl. No.: 689,158

[22] Filed: May 24, 1976

[51] Int. Cl.² ............................................. A12K 1/08
[52] U.S. Cl. ........................................ 426/31; 426/41; 426/53; 426/60; 426/69; 195/82
[58] Field of Search ............ 426/18, 31, 56, 53, 426/52, 49, 60, 62, 69, 41, 635, 656; 195/82, 96, 111, 32

[56] References Cited

U.S. PATENT DOCUMENTS

| 2,505,360 | 4/1950 | Jeffreys | 195/109 |
| 3,818,109 | 6/1974 | Bechtle | 426/41 |

*Primary Examiner*—R. B. Penland
*Attorney, Agent, or Firm*—Robert Brown, Jr.

[57] ABSTRACT

A method of producing an animal food supplement by growing a yeast that utilizes lactose on a mixture of wheat bran or husks from different grains which are mixed with dried whey, moistened with water, cooled and inoculated with yeast, a dairy culture used in making buttermilk, and *Lactobacillus acidophilus*, placed on perforated trays, then incubated for 12 to 24 hours at 27° to 34° C. and dried at 43° C. and lower.

6 Claims, No Drawings

ANIMAL FEED YEAST SUPPLEMENT FROM DRIED WHEY YEAST BRAN PROCESS

This invention relates to a process for producing an animal feed from whey rich in unidentified growth factors (UGF), animal protein factor (APF), whey factor and associated beneficial lactobacillus.

Whey is a by-product of the production of cheese, cottage cheese and casein from milk. Whey contains 4.8% lactose and only 0.8% protein. At the present time there are over 20 billion pounds of whey being produced per year in the U.S. and one-half of this is dumped into sewers and rivers creating a pollution problem.

Some of the whey is dried and is used mostly as a feed supplement. Its use as a feed is limited because of its laxative effect and low protein content.

Commercial fermentation processes have been developed for growing a special yeast in the liquid whey to produce cell protein. These methods, although excellent to produce protein for human needs, are not economically feasible for animal feeds.

We have now found that yeast protein and associated beneficial growth factors can be produced from the lactose of dried whey by growing a special yeast that utilizes lactose on a moist mixture of grain husks and dried whey. By this method, two to three times as much yeast solids are produced per unit of weight of substrate than in a liquid fermentation method. We also find that this type of yeast grows symbiotically with beneficial lactics without inhibiting yeast growth.

The types of yeast most efficient for rapid utilization of lactose are *Kluyveromyces fragilis* and *Kluyveromyces lactis*. Other yeast that utilize lactose can be used such as *Torulopsis cremoris* and *Torulopsis spherica*. *Kluyveromyces fragilis* was used as this organism gives the most efficient conversion of whey to protein.

The maximum number of yeast cells that can be produced in a conventional liquid whey fermentation method using a normal whey of 4.8% lactose is 5 billion/ml or $5 \times 10^9$, the number of yeast cells that can be grown on a solid substrate of wheat bran and whey can be as high as $1.8 \times 10^{10}$, or 18 billion per gram. There is an additional advantage to the semi-solid substrate process. The yeast cells grow symbiotically with the lactic acid producing organisms. The lactic count averages more than 1 per gram. A conventional liquid method with an abundance of air retards the growth of lactics.

The yeast cells and the lactics grow in a thin film over each bran particle.

The solid substrate should consist preferably of the husks from the various cereal grains; these are known as wheat bran, rice bran, oat hulls, soybean hulls, etc. The husks (or bran) acts as a carrier for the dissolved dried whey, minerals and other essential nutrients.

A substrate mixture is made of the following composition based on the total dry weight. The function of each ingredient is described.

Grain husks or bran are employed in amounts within the range of 80 to 87% to provide a natural air pervious surface for the growth of yeast and lactics. Wheat Red Dog is employed in amounts within the range of 2 to 5%. The Red Dog ingredient is a fraction consisting primarily of a mixture of the inner coating of the wheat husks and wheat flour; it supplies starch that is easily hydrolyzed. Fishmeal is employed in amounts within the range of one to two percent to provide a source of essential amino acids. Dried whey, typically containing 65 to 75% lactose, is employed in amounts within the range of 10 to 21%. The amount of lactose provided by the whey determines the amount of yeast solids that can be produced. We find that 21% dried whey in the dry ingredient formula is the upper limit for efficient and economical production of yeast. This would provide 14% lactose which in turn would yield 28% live yeast solids at 72% moisture. Urea is employed in amounts within the range of 0.1 to 0.3% to supply the nitrogen needed by the yeast cells to make their protein. Although some protein and non-protein nitrogen is present in the bran, the nitrogen of the urea is immediately available to the yeast and thus permits faster growth. The amount of urea depends on the amount of lactose present in the whey. Monocalcium phosphate is employed in amounts within the range of 2 to 2½%. This ingredient provides not only phosphate but also regulates the pH of the substrate from 4 to 4.5. Dried Kelp is employed in amounts within the range of 0.1 to 0.3%. This is a nutrient bearing sea plant that provides trace minerals. Other trace nutrients can be added especially when some particular nutrient deficient husks like rice hulls may require a supplement. Such supplementing nutrients are available in brewers yeast extracts, amino acids from protein hydrolysates, and Mozade (A dried fungal extract of Aspergillus oryzae).

To 100 parts of the above substrate mixture is added 70 to 80 parts water by weight, thereby providing watersubstrate ratios of 70/100 and 80/100, respectively. The moistened substrate is then steam-cooked at 100° C, while being mixed at atmospheric conditions for 10 to 25 minutes. It is then cooled to 35° C.

A suspension of seed yeast is prepared in sufficient water to make the total moisture of the mix approximately 40 to 60%. The amount of moisture depends on the type of husk used in the substrate because of differences in physical character. Some grain husks absorb more water than others.

The amount of seed yeast to use (based on the dry substrate) is 0.25 to 1.0% of compressed yeast. Compressed yeast is standardized and is expressed throughout this patent application as having 72% moisture. Dry yeast on an equivalent potency can be used (0.6 to 2%). In lieu of compressed or dry yeast, an active ferment of *K. fragilis* can be used to inoculate the semi-solid substrate. The amount used as an inoculum being an amount that contains the required amount of yeast solids expressed above. The increased moisture being added by a typical active ferment (which may be 3 to 10% compressed yeast solids) is taken into consideration as being a fraction of the total formula water expressed above. Included in the yeast inoculating suspension is a small amount of a beneficial lactic acid producing bacteria culture. About 0.025 to 0.05% of lactic culture (based on the total weight of the substrate) is used. The lactic culture can preferably be a cultured buttermilk or a pure milk culture of any special lactic desired such as: *Lactobacillus acidophilus, Lactobacillus bulgaricus, Lactobacillus thermophilus, Streptococcus lactis, Streptococcus cremoris,* etc.

After thorough mixing, the blend of substrate and inocula is spread on perforated trays at a depth of 1 inch to 3 inches depending on the density of the mixture and physical character of the grain husks. A more fluffy, porous mixture can be put on the trays at a greater depth. The trays are put in racks and placed in a chamber or room in which the temperature and moisture of the air is controlled as desired. Incubation is started at 30° to 32° C, a suitable temperature for yeast growth, and a relative humidity of 80 to 100% to prevent excessive drying of the substrate. Growth is completed in 12 to 24 hours. The yeast containing trays are then placed in a drying room and dried at a temperature of 38° to 43° C. The relative humidity of the air in the drying room should be held below 40% to permit fast drying so that the temperature of the material remains relatively cool and preferably lower than 38° C.

In lieu of using this method, the mixture of substrate and inocula can be made and cultured as described in my continuous tray method of culturing mold enzymes, U.S. Pat. No. 2,505,360.

The invention is further described in detail in the following examples:

EXAMPLE NO. I

A substrate was made as follows:

| | |
|---|---|
| 351.08 g | Wheat Bran |
| 40.0 g | Dried Whey |
| 8.0 g | Monocalcium Phosphate |
| 0.8 g | Urea |
| 0.12 g | Dried Kelp |

To this was added 200 ml water and thoroughly mixed, thereby providing a water/substrate ratio of 50/100. It was then placed in an open mixer and steamed directly for 15 minutes. This was then cooled to 40° C. The pH was adjusted with $H_2SO_4$ to 4.5. To 180 cc water was added 2 g of compressed *K. fragilis* yeast and 5 ml cultured buttermilk. This mixture was then added to the cooled bran mixture and mixed well, then placed on perforated trays at 1½ inches in depth. The trays were then placed in a incubator in which the humidity and temperature is automatically controlled. Temperature was regulated at 32° C and a humidity of about 85%. After 24 hours, the culture was dried in a special dryer at 110° F. The dried culture assayed 10 Billion ($1 \times 10^{10}$) yeast cells per gram. The dried culture assayed 1.2 Billion ($1.2 \times 10^9$) lactics.

EXAMPLE NO. 2

This example illustrates how a *K. fragilis* yeast culture may be produced for use in improving nutrition and affording basic nutrients to growing broilers.

A substrate was prepared as follows:

| | |
|---|---|
| 4010 g | Wheat Bran |
| 650 g | Dried Whey |
| 100 g | Monocalcium phosphate |
| 50 g | Mozyme (A fungal culture of *Aspergillus oryzae* grown on wheat bran |
| 5 g | Dried Kelp |
| 15 g | Urea |
| 10 g | Ammonium sulphate |
| 100 g | Wheat Red Dog |
| 60 g | Menhaden Fish Meal |
| 5000 g | |

To this above mix, 2500 ml water was added and mixed well, thereby providing a water/substrate ratio of 50/100. The mixture was steamed for 15 minutes at 100° C and cooled to 37° C.

For inoculating, a suspension was made consisting of

| | |
|---|---|
| 1500 mls | warm water at 35° C |
| 50 grams | *K. fragilis* compressed yeast |
| 25 mls | Cultured Buttermilk |

This inoculum mixture was added to the cooled bran substrate mix, blended well, then spread on perforated trays 1½ inches in depth.

The culture was incubated in an incubator in which the temperature was controlled at 32° C with a relative humidity of 85%. The culture was not allowed to go over 35° C by controlling the cooling air flow. After incubating 24 hours the culture was dried with 43° C air temperature; material temperature remained 37° C or below while drying.

The dried culture assayed 12 Billion ($1.2 \times 10^{10}$) yeast cells per gram and 1.5 Billion ($1.5 \times 10^9$) lactics per gram.

EXAMPLE NO. 3

The following substrate mix was prepared

| | |
|---|---|
| 1200 lbs. | Wheat Bran |
| 10 lbs. | Mozyme (A dried fungal culture of *Aspergillus oryzae*) |
| 200 lbs. | Dried Whey |
| 26 lbs. | Monocalcium phosphate |
| 3 lbs. | Urea |
| 2 lbs. | Ammonium sulfate |
| 1½ lbs. | Dried Kelp |
| 1442.5 | |

To the above mix was added 100 gallons (800 lbs.) water, thereby providing a water/substrate ratio of 56.5/100.

After mixing the mixture was steamed at 100° C for 20 minutes at atmospheric pressure.

It was then cooled to 32° C and inoculated with 50 gallons active ferment mixture as follows:

12½ gallons of an 18 hour fragilis active ferment containing 8% yeast solids at 72% moisture or 8 lbs. compressed yeast solids or 2.25 lbs. of yeast solids on a dry basis.

5 Fl. Oz. cultured buttermilk 30 gallons water

The inoculum mixture was blended with the cooled substrate mixture and then was spread on trays 1½ inches deep. The trays were placed in movable racks, then put into an incubating chamber. The temperature of the air was maintained at 30° to 32° C, humidity at 80 to 85%. Flow of air per minute was ½ to 1 volume per volume of incubator space. The rate of air flow was controlled depending on the temperature rise produced by the metabolizing yeast, which produce much external heat as they grow. Growth was complete after 20 hours. The racks were then transferred to a drying chamber. The culture was dried under conditions which did not permit the culture material to exceed 43° C.

The dried culture assayed an excess of 18 Billion ($1.8 \times 10^{10}$) yeast cells per gram and 2.5 ($2.5 \times 10^9$) Billion lactics per gram.

What is claimed is:

1. A process for producing an animal feed supplement by growing a yeast that utilizes lactose, which comprises the steps of
   a. preparing a solid substrate mixture composed of bran husks supplemented with essential nutrients, and 10 to 21% dried whey typically containing 65 to 75% lactose;

b. moistening said mixture to bring the water-substrate ratio within the range of 50/100 to 70/100, thereby providing a semi-solid substrate;

c. pasteurizing the moistened mixture and then cooling it to at least 100° F;

d. inoculating the cooled mixture with a lactose utilizing yeast selected from a group consisting of *Kluveromyces fragilis, Kluveromyces lactis, Torulopsis cremoris* and *Torulopsis spherica;* e. said lactose utilizing yeast being mixed with a lactic culture selected from a group consisting of Lactobacillus acidophilus, Lactobacillus bulgaricus, Lactobacillus thermophilus, Streptococcus cremoris, and Streptococcus lactis, and f. incubating the inoculated mixture at humidities and temperatures conducive to the growth of the yeast for 12 to 24 hours.

2. The process according to claim 1 wherein said nutrients are selected from a group consisting of urea, monocalcium phosphate, brewers yeast, yeast extract, and a fungal culture of *Aspergillus oryzae* grown on wheat bran.

3. The process according to claim 1 wherein said lactose-utilizing yeast is inoculated in the form of a compressed yeast suspended in water.

4. The process according to claim 1 wherein said lactose-utilizing yeast is inoculated in the form of an active fermenting yeast.

5. The process according to claim 1 wherein said inoculated substrate is formed in air-pervious layers, and wherein said layers are incubated at a temperature of 90° to 100° F. with a relative humidity of 80 to 90% while being aerated by a moderate air flow.

6. The process according to claim 1 wherein the incubated culture is dried at a temperature not exceeding 43° C.

* * * * *